United States Patent [19]

Takaya et al.

[11] Patent Number: 4,649,142
[45] Date of Patent: Mar. 10, 1987

[54] 3,4-DIHYDRO-1,3-DISUBSTITUTED-6-(SUBSTITUTED PHENYLIMINO)-2(1H)-PYRIMIDINONE USEFUL AS CARDIOTONIC AGENT AND ANTI-ALLERGIC AGENT

[75] Inventors: Takao Takaya, Kawanishi; Masayoshi Murata, Osaka; Kiyotaka Ito, Ibaragi, all of Japan

[73] Assignee: Fujisawa Pharmaceutical Co., Ltd., Osaka, Japan

[21] Appl. No.: 743,525

[22] Filed: Jun. 7, 1985

[30] Foreign Application Priority Data

Jun. 25, 1984 [GB] United Kingdom ............... 8416140
Sep. 17, 1984 [GB] United Kingdom ............... 8423438
Oct. 26, 1984 [GB] United Kingdom ............... 8427122

[51] Int. Cl.$^4$ ............... A61K 31/505; C07D 239/02
[52] U.S. Cl. ............................ 514/274; 544/316; 549/362; 549/469
[58] Field of Search ................ 544/316; 514/274

[56] References Cited

PUBLICATIONS

Fujisawa Pharmaceutical Co. Ltd., Chem. Abst. 102-95665g.

*Primary Examiner*—Donald G. Daus
*Assistant Examiner*—Cecilia Shen
*Attorney, Agent, or Firm*—Oblon, Fisher, Spivak, McClelland & Maier

[57] ABSTRACT

The invention relates to novel pyrimidinone compounds of anti-allergic and cardiotonic activity of the formula:

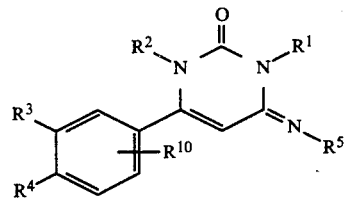

wherein
$R^1$ and $R^2$ are each lower alkyl, lower alkoxycarbonyl(lower)alkyl, carboxy(lower)alkyl or di(lower)alkylamino(lower)alkyl,
$R^3$ is hydroxy, lower alkoxy, halo(lower)alkoxy, lower alkylthio, lower alkanesulfinyl, lower alkanesulfonyl, nitro, amino or di(lower)alkanesulfonylamino,
$R^4$ is hydroxy, lower alkoxy, halo(lower)alkoxy, lower alkoxycarbonyl(lower)alkoxy or carboxy(lower)alkoxy, or
$R^3$ and $R^4$ are taken together to form lower alkylenedioxy or lower alkylidenedioxy,
$R^5$ is phenyl substituted with 1 to 4 substituents selected from the group consisting of lower alkyl and sulfamyl,
$R^{10}$ is hydrogen or sulfamyl, provided that when both of $R^1$ and $R^2$ are lower alkyl and $R^3$ and $R^4$ are lower alkoxy, then $R^{10}$ is sulfamoyl, and that when $R^3$ is hydroxy, then $R^4$ is hydroxy, and pharmaceutically acceptable salts thereof.

6 Claims, No Drawings

3,4-DIHYDRO-1,3-DISUBSTITUTED-6-(SUBSTITUTED PHENYLIMINO)-2(1H)-PYRIMIDINONE USEFUL AS CARDIOTONIC AGENT AND ANTI-ALLERGIC AGENT

This invention relates to new pyrimidinone derivatives. More particularly, this invention relates to new pyrimidinone derivatives and pharmaceutically acceptable salts thereof which have pharmacological activities, processes for preparation thereof, a pharmaceutical composition comprising the same and method of use thereof.

Accordingly, one object of this invention is to provide the new and useful pyrimidinone derivatives and pharmaceutically acceptable salts thereof.

Another object of this invention is to provide processes for preparation of the pyrimidinone derivatives and pharmaceutically acceptable salts thereof.

A further object of this invention is to provide a pharmaceutical composition comprising said pyrimidinone derivative or pharmaceutically acceptable salt thereof as a cardiotonic agent and anti-allergic agent.

Still further object of this invention is to provide a method of using said pyrimidinone derivative or a pharmaceutically acceptable salt thereof for therapeutic treatment of heart disease and allergic disease of human being and animals.

The pyrimidinone derivatives of this invention are novel and represented by the following general formula [I]:

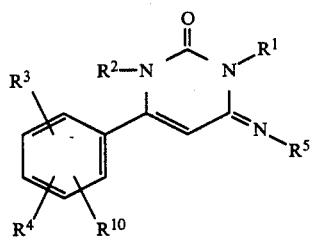

wherein
$R^1$ and $R^2$ are each lower alkyl, lower alkoxycarbonyl(lower)alkyl, carboxy(lower)alkyl or di(lower)alkylamino(lower)alkyl,
$R^3$ and $R^4$ are each hydroxy, lower alkoxy, halo(lower)alkoxy, lower alkylthio, lower alkanesulfinyl, lower alkanesulfonyl, nitro, amino, di(lower)alkanesulfonylamino, lower alkoxycarbonyl(lower)alkoxy or carboxy(lower)alkoxy, or
$R^3$ and $R^4$ are taken together to form lower alkylenedioxy or lower alkylidenedioxy,
$R^5$ is aryl optionally substituted with lower alkyl and/or sulfamoyl, and
$R^{10}$ is hydrogen or sulfamoyl, provided that when both of $R^1$ and $R^2$ are lower alkyl and $R^3$ and $R^4$ are lower alkoxy, then $R^{10}$ is sulfamoyl.

The object compound [I] and their salts of the present invention can be prepared by the following processes.

Process 1

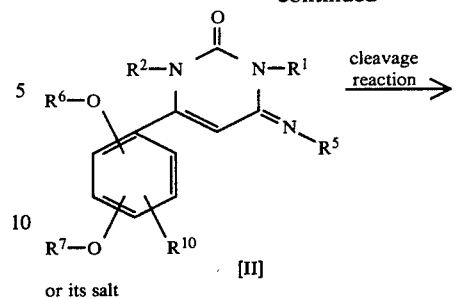

or its salt

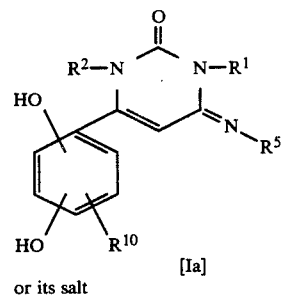

or its salt

Process 2

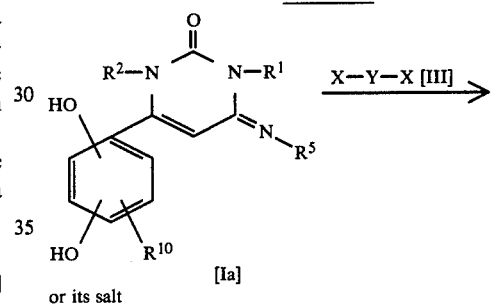

or its salt

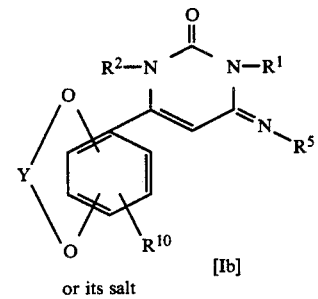

or its salt

Process 3

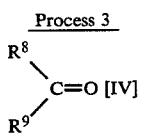

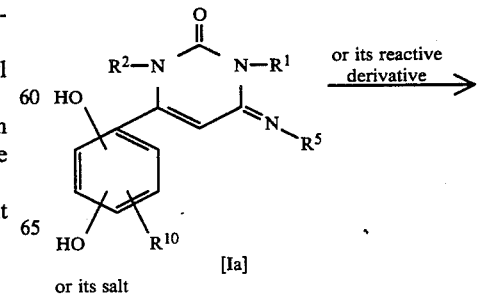

or its salt

-continued
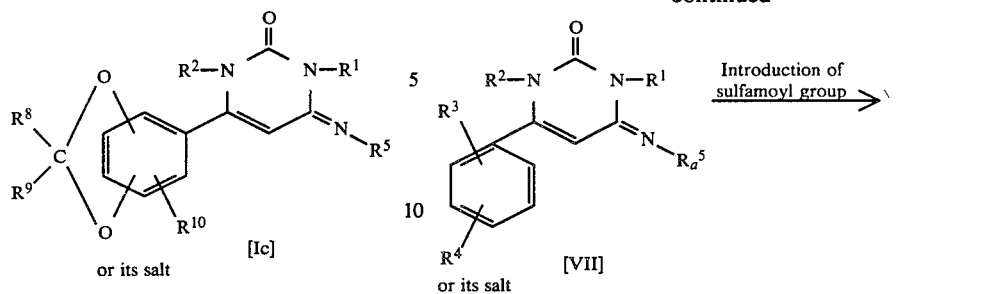
Process 4
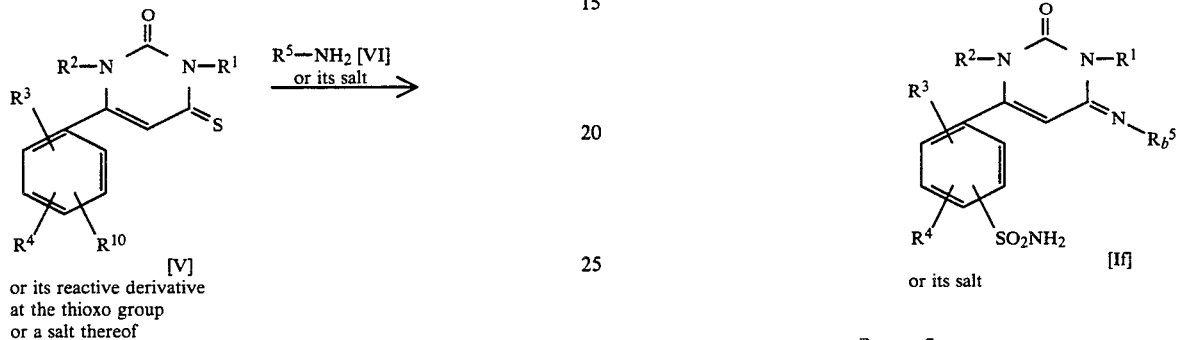
Process 5
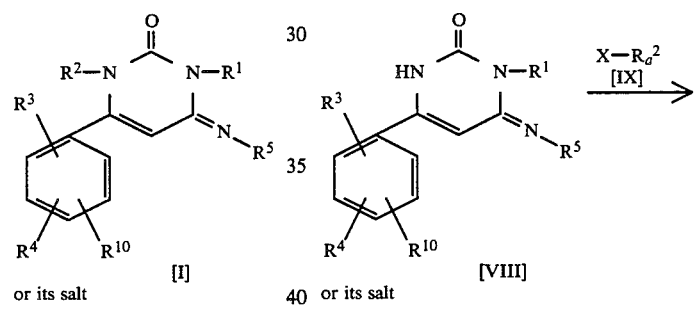
Process 6
-continued
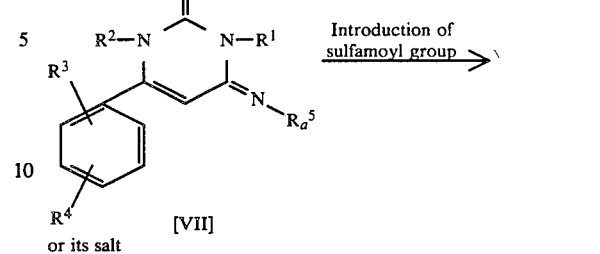
Process 7
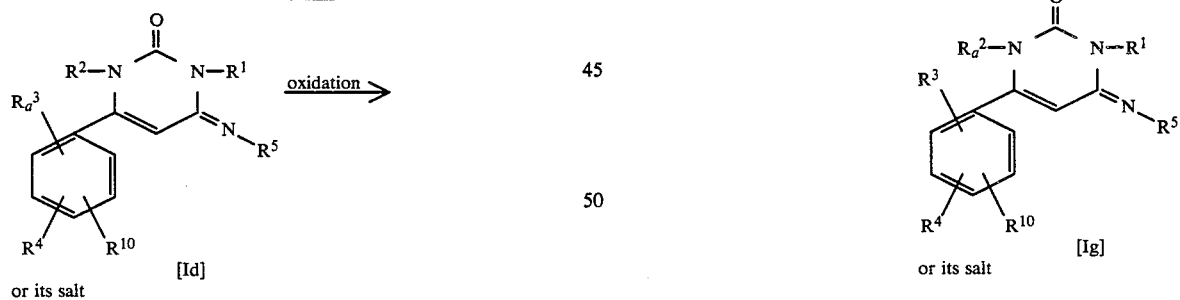
Process 8
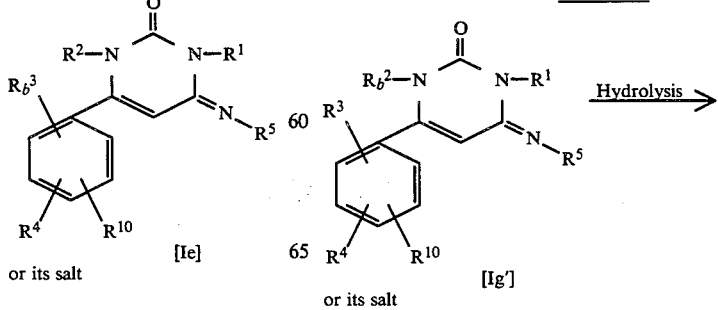

-continued
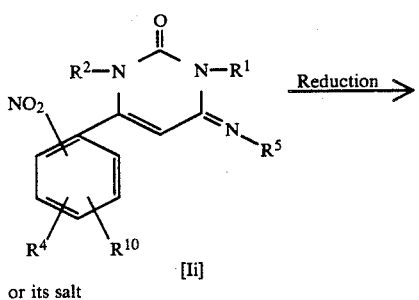
[Ih] or its salt
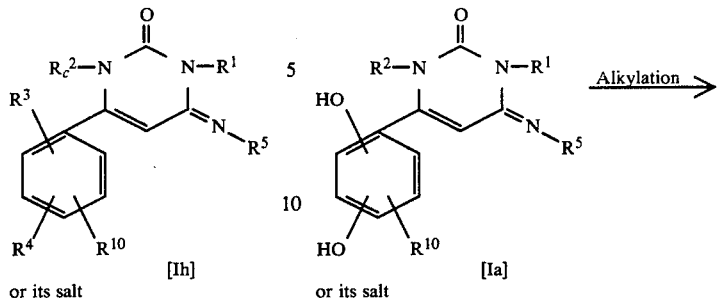
[Ia] or its salt
Process 9
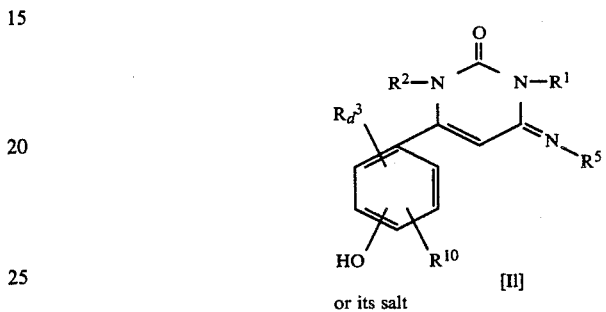
[Il] or its salt
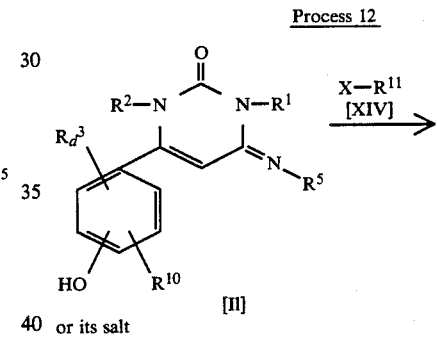
[Ii] or its salt
Process 12
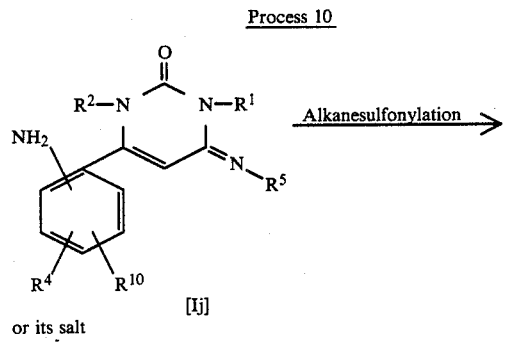
[Ij] or its salt
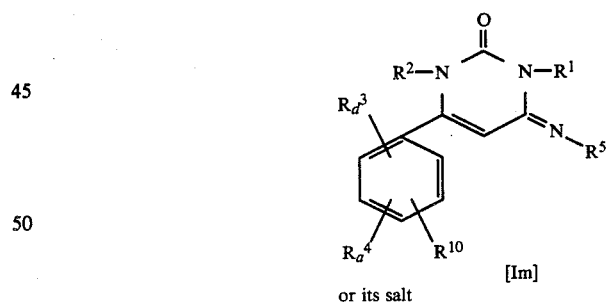
[Il] or its salt
Process 10
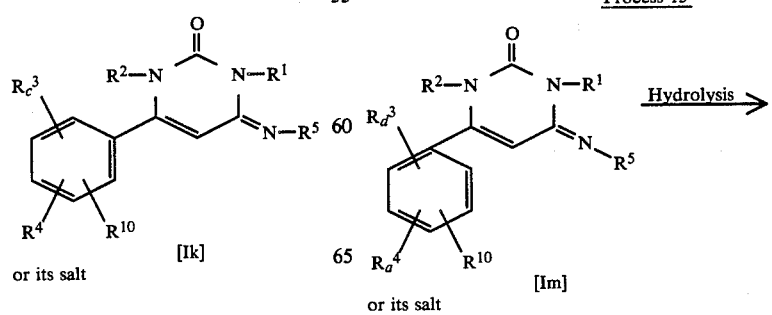
[Ij] or its salt
[Im] or its salt
Process 13
[Ik] or its salt
[Im] or its salt
Process 11

-continued

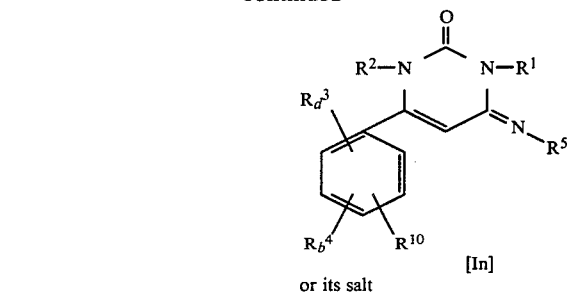

or its salt

Process 14

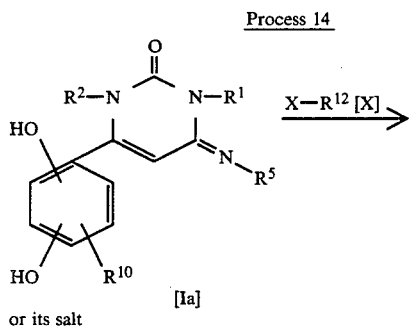

or its salt

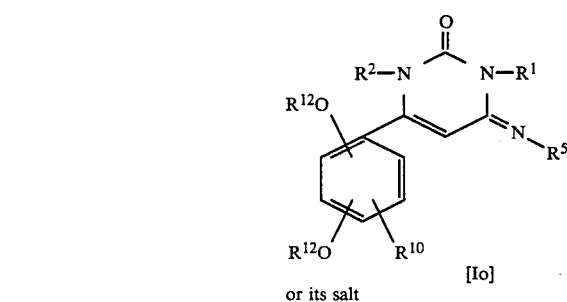

or its salt wherein
$R^1$, $R^2$, $R^3$, $R^4$, $R^5$ and $R^{10}$ are each as defined above,
$R_a{}^2$ is lower alkoxycarbonyl(lower)alkyl or di(lower-)alkylamino(lower)alkyl,
$R_b{}^2$ is lower alkoxycarbonyl(lower)alkyl,
$R_c{}^2$ is carboxy(lower)alkyl,
$R_a{}^3$ is lower alkylthio,
$R_b{}^3$ is lower alkanesulfinyl or lower alkanesulfonyl,
$R_c{}^3$ is di(lower)alkanesulfonylamino,
$R_d{}^3$ is lower alkoxy,
$R_a{}^4$ is lower alkoxycarbonyl(lower)alkoxy,
$R_b{}^4$ is carboxy(lower)alkoxy,
$R_a{}^5$ is aryl optionally substituted with lower alkyl,
$R_b{}^5$ is aryl optionally substituted with lower alkyl and sulfamoyl,
$R^6$ and $R^7$ are each lower alkyl,
$R^8$ and $R^9$ are each hydrogen or lower alkyl,
$R^{11}$ is lower alkoxycarbonyl(lower)alkyl,
$R^{12}$ is halo(lower)alkyl,
X is a leaving group, and
Y is lower alkylene or lower alkylidene.

Among the starting compounds, some of the compound [V] is novel and can be prepared by the following processes.

Process A

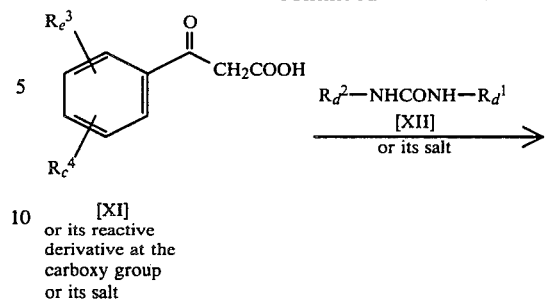

[XI]
or its reactive
derivative at the
carboxy group
or its salt $R_d{}^2$—NHCONH—$R_d{}^1$
[XII]
or its salt

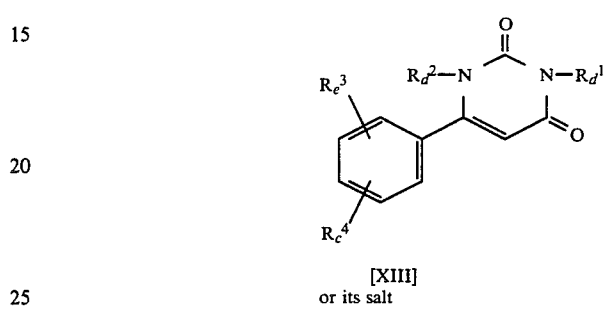

[XIII]
or its salt

Process B

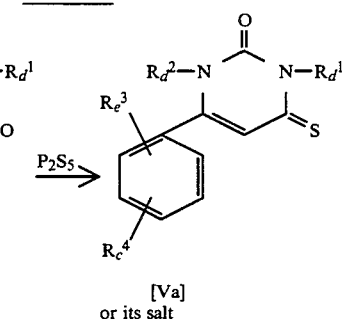

[XIII]              [Va]
or its salt         or its salt wherein $R_d{}^1$ and $R_d{}^2$ are each lower alkyl, $R_e{}^3$ is lower alkylthio or nitro and $R_c{}^4$ is lower alkoxy.

In the above and subsequent description of the present specification, suitable examples and illustrations for the various definitions to be included within the scope of the invention are explained in detail as follows:

The term "lower" is intended to mean 1 to 6 carbon atom(s) unless otherwise indicated.

Suitable examples of the lower alkyl for $R^1$, $R^2$, $R_d{}^1$, $R_d{}^2$, $R^6$, $R^7$, $R^8$ and $R^9$ may be a straight or branched one such as methyl, ethyl, propyl, isopropyl, butyl, isobutyl, tert-butyl, pentyl, hexyl or the like.

Suitable example of "lower alkyl" moiety in the terms "lower alkoxycarbonyl(lower)alkyl", "carboxy(lower-)alkyl", "di(lower)alkylamino(lower)alkyl", "lower alkylthio", "lower alkanesulfinyl", "lower alkanesulfonyl", "halo(lower)alkyl" and "aryl optionally substituted with lower alkyl" can be referred to the ones as exemplified above.

Suitable example of "lower alkoxycarbonyl" moiety in the terms "lower alkoxycarbonyl(lower)alkyl" and "lower alkoxycarbonyl(lower)alkoxy" may include ones having 2 to 7 carbon atoms such as methoxycarbonyl, ethoxycarbonyl, propoxycarbonyl, isopropoxycarbonyl, butoxycarbonyl, t-butoxycarbonyl, pentyloxycarbonyl, hexyloxycarbonyl or the like.

Suitable example of "lower alkoxy" and "lower alkoxy" moiety in the terms "halo(lower)alkoxy", "lower alkoxycarbonyl(lower)alkoxy" and "carboxy(lower)alkoxy" may include methoxy, ethoxy, propoxy, isopropoxy, butoxy, t-butoxy, pentyloxy, hexyloxy and the like.

Suitable example of "di(lower)alkanesulfonylamino" may include dimethanesulfonylamino, diethanesulfonylamino, dipropanesulfonylamino, dibutanesulfonylamino, dipentanesulfonylamino, dihexanesulfonylamino and the like.

Suitable example of "halo(lower)alkoxy" may include "monohalo(lower)alkoxy" (e.g. chloromethoxy, bromomethoxy, fluoromethoxy, etc.), "dihalo(lower)alkoxy" (e.g. dichloromethoxy, dibromomethoxy, difluoromethoxy, etc.), "trihalo(lower)alkoxy" (e.g. trichloromethoxy, tribromomethoxy, trifluoromethoxy, trifluoroethoxy, etc.) and the like.

Suitable example of "halo(lower)alkyl" may include "monohalo(lower)alkyl" (e.g. chloromethyl, bromomethyl fluoromethyl, etc.), "dihalo(lower)alkyl" (e.g. dichlomethyl, dibromomethyl, difluoromethyl, etc.) and "trihalo(lower)alkyl" (e.g. trichloromethyl, tribromomethyl, trifluoromethyl, trifluoroethyl, etc.) and the like.

Suitable examples of the lower alkylene group for Y may be a straight or branched one such as methylene, ethylene, trimethylene, tetramethylene, pentamethylene, hexamethylene, propylene, ethylethylene, propylethylene, isopropylethylene, methylpentamethylene or the like.

The lower alkylenedioxy formed by $R^3$ and $R^4$ is the group represented by the formula "-O-(lower)alkylene-O-", wherein the lower alkylene moiety can be referred to those as exemplified in the above.

Suitable examples of the lower alkylidene group for Y may include methylene, ethylidene, propylidene, isopropylidene, butylidene, sec-butylidene, isobutylidene, hexylidene, isohexylidene and the like.

The lower alkylidenedioxy formed by $R^3$ and $R^4$ is the group represented by the formula

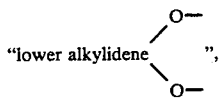

wherein the lower alkylidene moiety can be referred to those as exemplified in the above.

Suitable examples of the aryl group may include phenyl, naphthyl and the like. These aryl groups may be optionally substituted with one or more lower alkyl group(s) as exemplified above, and/or sulfamoyl.

Suitable examples of the aryl group having such substituent(s) may include p-tolyl, o-tolyl, m-tolyl, 4-ethylphenyl, 4-hexylphenyl, 2,6-dimethylphenyl, 3,4-dimethylphenyl, xylyl, mesityl(2,4,6-trimethylphenyl), 3-sulfamoyl-2,4,6-trimethylphenyl, 3-sulfamoyl-2,6-dimethylphenyl, 4-sulfamoyl-2,3-dimethylphenyl, 3-sulfamoyl-2-methylphenyl, 4-sulfamoyl-3-methylphenyl, and the like.

Suitable examples of the leaving group for X may be halide [e.g. chloride, bromide, iodide, etc.], sulfonate [e.g. methanesulfonate, benzenesulfonate, toluenesulfonate, etc.] or the like.

Suitable pharmaceutically acceptable salts of the object compound [I] are conventional non-toxic salts and include a metal salt such as an alkali metal salt [e.g. sodium salt, potassium salt, etc.] and an alkaline earth metal salt [e.g. calcium salt, magnesium salt, etc.], an ammonium salt, an organic base salt [e.g. trimethylamine salt, triethylamine salt, pyridine salt, picoline salt, dicyclohexylamine salt, N,N'-dibenzylethylenediamine salt, etc.], an organic acid salt [e.g. formate, acetate, trifluoroacetate, maleate, tartrate, methanesulfonate, benzenesulfonate, toluenesulfonate, etc.], an inorganic acid salt [e.g. hydrochloride, hydrobromide, sulfate, phosphate, etc.], a salt with an amino acid [e.g. arginine salt, ornithine salt, etc.], and the like.

In this respect, it is to be noted that the compounds [Ia] to [Io] are included within the scope of the compound [I], and accordingly the suitable salts of these compounds [Ia] to [Io] are to be referred to those as exemplified for the object compound [I] in the above.

The processes for preparing the object compound [I] and salts thereof are explained in detail in the following.

Process 1

The object compound [Ia] or its salt can be prepared by subjecting the compound [II] or its salt to a cleavage reaction of the lower alkyl groups for $R^6$ and $R^7$.

Suitable salts of the compound [II] may be the same as those exemplified for the compound [I].

This reaction is usually conducted in the presence of a cleavage reagent.

Suitable examples of the cleavage reagents may be Lewis acid such as boron trihalide [e.g. boron trichloride, boron tribromide, boron triiodide, boron trifluoride, boron trifluoride ethyl etherate, etc.], titanium tetrahalide [e.g. titanium tetrachloride, etc.], tin tetrahalide [e.g. tin tetrabromide, etc.], aluminum halide [e.g. aluminum chloride, etc.], hydrohalogenic acid (e.g. hydrobromic acid, etc.) or the like;

a combination of the abovementioned Lewis acid and thiol compound [e.g. methanethiol, ethanethiol, benzenethiol, etc.];

silane compound [e.g. iodotrimethylsilane, etc.];

thiolate compound [e.g. sodium ethanethiolate, potassium benzenethiolate, sodium thiocresolate, etc.];

a mixed acid of hydrogen halide [e.g. hydrogen chloride, hydrogen bromide, etc.] and an organic acid [e.g. trifluoroacetic acid, acetic acid, etc.]; or the like.

This reaction is usually carried out in a conventional solvent such as water, methanol, ethanol, propanol, tetrahydrofuran, dioxane, chloroform, methylene chloride, dimethylformamide, dimethyl sulfoxide or any other organic solvent which does not adversely influence the reaction.

The reaction temperature is not critical, and the reaction can be carried out under cooling to heating.

Process 2

The object compound [Ib] or its salt can be prepared by reacting the compound [Ia] or its salt with the compound [III].

This reaction is preferably conducted in the presence of a base such as alkali metal hydride [e.g. sodium hydride, potassium hydride, etc.], alkaline earth metal hydride [e.g. calcium hydride, magnesium hydride, etc.], alkali metal hydroxide [e.g. sodium hydroxide, potassium hydroxide, etc.], alkali metal carbonate [e.g. sodium carbonate, potassium carbonate, etc.], alkali metal bicarbonate [e.g. sodium bicarbonate, potassium bicarbonate, etc.], alkali metal fluoride [e.g. potassium fluoride, cesium fluoride, etc.], alkali metal alkoxide [e.g. sodium methoxide, sodium ethoxide, potassium tert-butoxide, etc.] or the like.

This reaction is usually carried out in a conventional solvent such as water, methanol, ethanol, propanol, tetrahydrofuran, dioxane, acetonitrile, methylene chloride, chloroform, benzene, dimethylformamide, dimethyl sulfoxide or any other organic solvent which does not adversely influence the reaction. These solvents can be optionally selected according to the kinds of the starting compound [Ia], the compound [III] and the base to be used. In case that the compound [III] is liquid, it can be also used as a solvent.

The reaction temperature is not critical, and the reaction can be carried out under cooling to heating.

Process 3

The object compound [Ic] or its salt can be prepared by reacting the compound [Ia] or its salt with the compound [IV] or its reactive derivative at the carbonyl group.

The reactive derivatives at the carbonyl group of the compound [IV] may include aldehyde acetal derivative, ketone acetal derivative and the like. Suitable examples of the compound [IV] in a form of such reactive derivative may be di(lower)alkoxysubstituted lower alkane such as dimethoxymethane, diethoxymethane, 1,1-dimethoxyethane, 1-ethoxy-1-methoxyethane, 2,2-dimethoxypropane, 2,2-diethoxypropane, 2-ethoxy-2-methoxypropane, 2,2-dimethoxybutane or the like.

The reaction is preferably conducted in the presence of a catalyst such as hydrohalogenic acid [e.g. hydrochloric acid, hydrobromic acid, etc.], sulfonic acid [e.g. p-toluenesulfonic acid, benzenesulfonic acid, etc.], zinc halide [e.g. zinc chloride, etc.], tin tetrahalide [e.g. tin tetrachloride, etc.], ferric halide [e.g. ferric chloride, etc.], cation exchange resin (acid type) [e.g. sulfonated polystyrene resin, etc.], or the like.

The reaction can also be conducted under dehydrating condition such as an azeotropic dehydration, in the presence of a dehydrating agent [e.g. anhydrous magnesium sulfate, anhydrous zinc chloride, phosphorus pentoxide, anhydrous cupric sulfate, zeolite, silica gel, etc.] or the like.

This reaction is usually carried out in a conventional solvent such as methanol, ethanol, tetrahydrofuran, dioxane, methylene chloride, chloroform, benzene, dimethylformamide, dimethyl sulfoxide or any other organic solvent which does not adversely influence the reaction.

The reaction temperature is not critical, and the reaction can be carried out under cooling to heating.

Process 4

The object compound [I] or its salt can be prepared by reacting the compound [V] or its reactive derivative at the thioxo group or a salt thereof with the compound [VI] or its salt.

Suitable salts of the compounds [V] and [VI] can be referred to those as exemplified for the compound [I].

Suitable reactive derivative at the thioxo group of the compound [V] may be S-alkyl derivative [e.g. S-methyl derivative, S-ethyl derivative, S-octyl derivative, etc.], S-ar(lower)alkyl derivative [e.g. S-benzyl derivative, etc.] or the like. These reactive derivatives can be prepared by reacting the compound [V] or its salt with an alkylating agent such as alkyl halide [e.g. methyl iodide, ethyl iodide, octyl bromide, etc.], ar(lower)alkyl halide [e.g. benzyl chloride, benzyl bromide, etc.] or the like.

The present reaction is usually carried out in a conventional solvent such as methanol, ethanol, propanol, tetrahydrofuran, dioxane, methylene chloride, dimethylformamide or any other organic solvent which does not adversely influence the reaction. In case that the compound [VI] is liquid, it can also be used as a solvent.

The reaction temperature is not critical, and the reaction is usually carried out at ambient temperature or under warming or heating.

Process 5

The compound [Ie] or its salt can be prepared by oxidizing the compound [Id] or its salt.

The present oxidation reaction can be carried out by a conventional method which is applied for the transformation of —S— into —SO— or —SO$_2$—, for example by using an oxidizing agent such as m-chloroperbenzoic acid, perbenzoic acid, peracetic acid, ozone, hydrogen peroxide, periodic acid or the like.

The present reaction is usually carried out in a solvent such as water, acetone, dioxane, acetonitrile, dimethylformamide, chloroform, methylene chloride, ethyl acetate or any other solvents which do not adversely affect the reaction.

The reaction temperature is not critical, and the reaction is preferably carried out under cooling or at ambient temperature.

In case that the compound having —SO— group and the one having —SO$_2$— group are formed in the course of the reaction, these two compounds can be separated according to a conventional method.

Process 6

The compound [If] or its salt can be prepared by subjecting the compound [VII] or its salt to introduction reaction of sulfamoyl group.

Suitable salt of the compound [VII] can be referred to the ones as exemplified for the compound [I].

The present reaction can be carried out by reacting the compound [VII] or its salt with introducing agent of sulfamoyl group.

Suitable introducing agent may include a combination of halosulfonic acid (e.g. chlorosulfonic acid, bromosulfonic acid, etc.) and ammonia and the like.

The reaction can be carried out with or without solvent.

The reaction temperature is not critical and the reaction is preferably carried out under cooling to warming.

Process 7

The compound [Ig] or its salt can be prepared by reacting the compound [VIII] or its salt with the compound [IX].

Suitable salt of the compound [VIII] can be referred to the ones as exemplified for the compound [I].

The reaction is usually carried out in a solvent such as N,N-dimethylformamide, acetone or any other solvent which does not adversely affect the reaction.

The reaction is preferably carried out in the presence of a base as mentioned above for Process 2.

The reaction temperature is not critical and the reaction is preferably carried out under cooling to heating.

Process 8

The compound [Ih] or its salt can be prepared by subjecting the compound [Ig'] or its salt to hydrolysis reaction.

The present hydrolysis reaction can be carried out by reacting the compound [Ig'] or its salt with a base or an acid.

Suitable base may include an inorganic base and an organic base such as an alkali metal (e.g. sodium, potassium, etc.), an alkaline earth metal (e.g. magnesium, calcium, etc.), the hydroxide or carbonate or bicarbonate thereof, trialkylamine (e.g. trimethylamine, triethylamine, etc.), picoline, 1,5-diazabicyclo[4,3,0]non-5-ene, 1,4-diazabicyclo-[2,2,2]octane, 1,5-diazabicyclo[5,4,0]undecene-5, or the like.

Suitable acid may include an organic acid (e.g. formic acid, acetic acid, propionic acid, trifluoroacetic acid, etc.) and an inorganic acid (e.g. hydrochloric acid, hydrobromic acid, sulfuric acid, etc.).

The reaction is usually carried out in a solvent such as water, an alcohol (e.g. methanol, ethanol, etc.), a mixture thereof or any other solvent which does not adversely influence the reaction. A liquid base or acid can also be used as the solvent.

The reaction temperature is not critical and the reaction is usually carried out under cooling to warming.

Process 9

The compound [Ij] or its salt can be prepared by subjecting the compound [Ii] or its salt to reduction.

The reduction method applicable for the present reduction may include, for example, reduction by using a combination of a metal (e.g. zinc, zinc amalgam, etc.) or a salt of chrome compound (e.g. chromous chloride, chromous acetate, etc.) and an organic or inorganic acid (e.g. acetic acid, propionic acid, hydrochloric acid, etc.); conventional catalytic reduction in the presence of a conventional metallic catalyst (e.g. palladium-carbon, Raney nickel, etc.); reduction using alkali metal borohydride (e.g. sodium borohydride, potassium borohydride, etc.) or the like.

The reaction conditions of the present reduction can be referred to the conventional ones.

Process 10

The compound [Ik] or its salt can be prepared by subjecting the compound [Ij] or its salt to alkanesulfonylation reaction.

The present reaction can be carried out by reacting the compound [Ij] or its salt with alkanesulfonylating agent.

Suitable said agent may include lower alkanesulfonic acid represented by the formula:

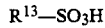

$R^{13}-SO_3H$ wherein $R^{13}$ is lower alkyl and its reactive derivatives at the sulfo group.

Suitable reactive derivatives at the sulfo group may include acid halide (e.g. acid chloride, acid bromide, etc.), acid anhydride, activated ester, activated amide and the like.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvent which does not adversely influence to the reaction. Among these solvents, hydrophilic solvents may be used in a mixture with water.

When the lower alkanesulfonic acid is used in free acid form in the reaction, the reaction is preferably carried out in the presence of a conventional condensing agent such as N,N-dicyclohexylcarbodiimide; phosphorus oxychloride; phosphorus trichloride; phosphorus pentachloride; thionyl chloride; oxalyl chloride; 1-(p-chlorobenzenesulfonyloxy)-6-chloro-1H-benzotriazole; so-called Vilsmeier reagent, for example (chloromethylene) dimethylammonium chloride produced by the reaction of dimethylformamide with thionyl chloride or phosgene, a compound produced by the reaction of dimethylformamide with phosphorus oxychloride, etc.; or the like.

The reaction may be also carried out in the presence of an inorganic or an organic base as exemplified above.

The reaction temperature is not critical and the reaction is preferably carried out at ambient temperature, under warming or heating.

Process 11

The compound [Il] or its salt can be prepared by subjecting the compound [Ia] or its salt to alkylation reaction.

The alkylating agent to be used in the present alkylation reaction may include di(lower)alkyl sulfate (e.g. dimethyl sulfate, diethyl sulfate, etc.), diazo(lower)alkane (e.g. diazomethane, diazoethane, etc.), lower alkyl halide (e.g. methyl iodide, ethyl iodide, etc.), lower alkyl sulfonate (e.g. methyl p-toluenesulfonate, etc.), and the like.

The reaction using di(lower)alkyl sulfate, lower alkyl halide or lower alkyl sulfonate is usually carried out in a solvent such as water, acetone, ethanol, ether, dimethylformamide or any other solvent which does not adversely influence the reaction. The present reaction is preferably carried out in the presence of a base such as an inorganic base or an organic base as aforementioned. The reaction temperature is not critical and the reaction is usually carried out under cooling to heating around boiling point of the solvent.

The reaction using diazoalkane is usually carried out in a solvent such as ether, tetrahydrofuran or the like. The reaction temperature is not critical and the reaction is usually carried out under cooling or at ambient temperature.

Process 12

The compound [Im] or its salt can be prepared by reacting the compound [Il] or its salt with the compound [XIV].

The present reaction can be carried out in substantially the same manner as that of Process 7.

Process 13

The compound [In] or its salt can be prepared by subjecting the compound [Im] or its salt to hydrolysis reaction.

The present reaction can be carried out in substantially the same manner as that of Process 8.

Process 14

The compound [Io] or its salt can be prepared by reacting the compound [Ia] or its salt with the compound [X]. The reaction is preferably carried out in the presence of a base as mentioned above for Process 2.

This reaction is usually carried out in a conventional solvent such as water, methanol, ethanol, propanol, tetrahydrofuran, dioxane, acetonitrile, methylene chloride, chloroform, benzene, dimethylformamide, dimethyl sulfoxide or any other organic solvent which does not adversely influence the reaction.

The reaction temperature is not critical and the reaction is usually carried out under cooling to warming.

The processes for preparing the starting compound [Va] and its salt are explained in detail in the following.

Process A

The compound [XIII] or its salt can be prepared by reacting the compound [XI] or its reactive derivative at the carboxy group or its salt with the compound [XII] or its salt.

Suitable salts of the compounds [XIII], [XI] and [XII] can be referred to those as exemplified for the compound [I].

Suitable reactive derivative at the carboxy group of the compound [XI] may include an ester, an acid halide, an acid anhydride and the like, preferably lower alkyl ester.

This reaction is usually carried out in a conventional solvent such as water, methanol, ethanol, propanol, tetralin, tetrahydrofuran, dioxane, chloroform, toluene, dimethylformamide, dimethylsulfoxide or any other organic solvent which does not adversely influence the reaction.

This reaction is preferably conducted in the presence of an acid such as inorganic acid [e.g. hydrochloric acid, sulfuric acid, polyphosphoric acid, etc.], organic acid [e.g. trifluoroacetic acid, benzenesulfonic acid, toluenesulfonic acid, etc.] or the like.

The reaction can also be conducted under dehydrating condition such as an azeotropic dehydration, in the presence of a dehydrating agent [e.g. magnesium sulfate, anhydrous zinc chloride, phosphorus pentoxide, zeolite, silica gel, etc.] or the like.

In case that the compound [XI] is used in a free acid form or its salt form, the reaction is preferably carried out in the presence of a conventional condensing agent.

The reaction temperature is not critical, and the reaction is usually carried out at ambient temperature or under warming or heating.

Process B

The compound [Va] or its salt can be prepared by reacting the compound [XIII] or its salt with phosphorus pentasulfide.

This reaction is usually carried out in a conventional solvent such as benzene, toluene, xylene, pyridine, tetrahydrofuran, dioxane or any other organic solvent which does not adversely influence the reaction.

The reaction temperature is not critical, and the reaction is usually carried out under warming or heating.

The new pyrimidinone derivatives [I] and pharmaceutical acceptable salts thereof possess a cardiotonic activity and anti-allergic activity, and are useful for a therapeutic treatment of heart disease [e.g. cardiac insufficiency, etc.] and allergic disease [e.g. asthma etc.]

For the purpose of showing pharmaceutical activity of the pyrimidinone derivatives [I], cardiotonic test data and anti-SRS-A test data of the representative compounds of the pyrimidinone derivatives [I] are illustrated in the following.

(1) Cardiotonic activity (i) Test Method:

Mongrel dogs of either sex were anesthetized with sodium pentobarbital, 35 mg/kg, i.p.. The animals were allowed to breathe spontaneously. The left carotid artery was isolated and a catheter (USCI, #8F) filled with heparinized saline was inserted and advanced into the left ventricle. The catheter was connected to a pressure transducer (Nihonkohden, MPU-0.5A) to measure the left ventricular pressure, from which dp/dt max was derived by analog computing. To measure the systemic blood pressure the left femoral artery was cannulated. The blood pressure pulse was used to trigger a heart rate meter. Another catheter was positioned in the vena cava through right femoral vein for injection of drugs. Systemic blood pressure, left ventricular pressure, dp/dt max and heart rate were recorded simultaneously on a polygram (Nihonkohden, RJG-4008).

Test compound was dissolved in distilled water (0.2 ml/kg) or dimethyl sulfoxide (0.04 ml/kg) and injected into the femoral vein. The parameters after dosing were compared with those during the predosing period.

Test results were represented in terms of percentage of dp/dt max changes (dp/dt M.C.) calculated by following formula.

$$dp/dt \text{ M.C. } (\%) = \left( \frac{dp/dt \text{ max after dosing}}{dp/dt \text{ max before dosing}} - 1 \right) \times 100$$

(ii) Test Compounds:
(1) 3,4-Dihydro-6-(3,4-dihydroxyphenyl)-1-ethyl-3-methyl-4-(2,4,6-trimethylphenylimino)-2(1H)-pyrimidinone
(2) 3,4-Dihydro-6-(4-methoxy-3-methylsulfonylphenyl)-1,3-dimethyl-4-(2,4,6-trimethylphenylimino)-2(1H)-pyrimidinone (iii) Test Results:

| Test Compound | dp/dt M.C. (%) (Dose: 1.0 mg/kg) |
| --- | --- |
| 1 | 87% |
| 2 | 132% |

As being apparent from the above test result, the object compounds [I] of the present invention are useful as cardiotonic agents.

(2) Anti-SRS-A activity (i) Test method:

Peritoneal exudate cells were obtained from glycogen injected SD rats and adjusted to $1 \times 10^7$ cells/ml with Tyrode solution. One ml of cell suspension was incubated with indomethacin (10 μg/ml) and test compound for 10 min. followed by additional 10 min. incubation with $Ca^{++}$-ionphore (A23187, 1 μg/ml). Supernatant was collected by centrifugation and the SRS-A (slow-reacting-substance of anaphylaxis) activity was measured as the contractile activity on isolated guinea pig ileum in the presence of mepyramine, atropine and methysergid.

Test results were expressed in the terms of percentage of inhibition of SRS-A synthesis or release from peritoneal exudate cells.

(ii) Test Compound:
3,4-Dihydro-6-(3,4-dihydroxyphenyl)-1-ethyl-3-methyl-4-(2,4,6-trimethylphenylimino)-2(1H)-pyrimidinone.

(iii) Test Results:
Inhibition (%): 93%

As being apparent from the above test result, the object compounds [I] of the present invention are useful as anti-allergic agents.

For therapeutic administration, the object compounds [I] of the present invention and pharmaceutically acceptable salts thereof are used in a form of the conventional pharmaceutical preparation in admixture with a conventional pharmaceutically acceptable carrier such as an organic or inorganic solid or liquid excipient which is suitable for oral, parenteral or external administration. The pharmaceutical preparation may be compounded in a solid form such as granule, capsule, tablet, dragee or suppository, or in a liquid form such as solution, suspension or emulsion. If needed, there may be included in the above preparation auxiliary substance such as stabilizing agent, wetting or emulsifying agent, buffer or any other commonly used additives.

The effective ingredient may usually be administered with a unit dose of 0.01 mg/kg to 500 mg/kg, 1 to 4 times a day. However, the above dosage may be increased or decreased according to age, weight and conditions of the patient or the administering method.

The following preparations and examples are given only for the purpose of illustrating the present invention in more detail.

PREPARATION 1

To a mixture of ethyl 4'-methoxy-3'-methylthiobenzoacetate (3.5 g) and N,N'-dimethylurea (1.26 g) were added ethanol (0.4 ml) and conc hydrochloric acid (1 drop). The mixture was stirred under reduced pressure at 120° C. for 4.5 hours, and at 150° C. for more an hour. The resulting mass was dissolved in ethyl acetate, and washed with aqueous sodium bicarbonate solution. The organic layer was dried over sodium sulfate, and chromatographed on silica gel eluting with chloroform to give 1,3-dimethyl-6-(4-methoxy-3-methylthiophenyl)-1,2,3,4-tetrahydropyrimidine-2,4-dione (1.06 g). mp 148°–150° C.

IR (Nujol): 1700, 1655 cm$^{-1}$.

NMR (CDCl$_3$, δ): 7.3–6.7 (3H, m), 5.65 (1H, s), 3.83 (3H, s), 3.36 (3H, s), 3.22 (3H, s), 2.41 (3H, s).

PREPARATION 2

To a suspension of 1,3-dimethyl-6-(4-methoxy-3-methylthiophenyl)-1,2,3,4-tetrahydropyrimidine-2,4dione (6.5 g) in pyridine (60 ml) was added phosphorus pentasulfide (4.95 g), and refluxed for 8 hours. After cooled, the mixture was poured into water (600 ml). The precipitates were collected, dried in the air, and refluxed with ethanol (150 ml) for 2 hours. After cooled, resulting precipitates were filtered, and washed with ethanol and diisopropyl ether, to give 1,3-dimethyl-6-(4-methoxy-3-methylthiophenyl)-1,2,3,4-tetrahydro-4-thioxopyrimidin-2-one (5.47 g). mp 174°–176° C.

IR (Nujol): 1680, 1610 cm$^{-1}$.

NMR (CDCl$_3$, δ): 7.3–6.8 (3H, m), 6.62 (1H, s), 3.94 (3H, s), 3.82 (3H, s), 3.28 (3H, s), 2.43 (3H, s).

PREPARATION 3

To a solution of 1,3-dimethyl-6-(4-methoxyphenyl)-1,2,3,4-tetrahydropyrimidine-2,4-dione (4.4 g) in acetic acid (22 ml) were added conc.sulfuric acid (9 ml) and conc. nitric acid (18 ml) under ice-cooling. The mixture was stirred at 5°–10° C. for 1.5 hours and at ambient temperature further for 2 hours. The mixture was poured into ice-water, and stirred. After the aqueous mixture was neutralized with aqueous sodium hydroxide, the resultant precipitates were filtered. The precipitates were washed with water and dried in air to give 1,3-dimethyl-6-(4-methoxy-3-nitrophenyl)-1,2,3,4-tetrahydropyrimidine-2,4-dione (3.67 g).

m.p. 185°–188° C.

IR (Nujol): 1710, 1660 cm$^{-1}$.

NMR (CDCl$_3$, δ): 7.92 (1H, d, J=2 Hz), 7.66 (1H, dd, J=2 Hz, J=9 Hz), 7.35 (1H, d, J=9 Hz), 5.73 (1H, s), 4.06 (3H, s), 3.39 (3H, s), 3.29 (3H, s).

PREPARATION 4

The following compound was obtained according to a similar manner to that of Preparation 2. 1,3-Dimethyl-6-(4-methoxy-3-nitrophenyl)-1,2,3,4-tetrahydro-4-thioxopyrimidine-2-one.

m.p. 198°–203° C.

IR (Nujol): 1695, 1630 cm$^{-1}$.

NMR (DMSO-d$_6$, δ): 8.05 (1H, d, J=2 Hz), 7.82 (1H, dd, J=2 Hz, J=8 Hz), 7.47 (1H, d, J=8 Hz), 6.49 (1H, s), 4.01 (3H, s), 3.70 (3H, s), 3.19 (3H, s).

PREPARATION 5

To a solution of 6-(3,4-dimethoxyphenyl)-1,3-dimethyl-1,2,3,4-tetrahydropyrimidine-2,4-dione (2.0 g) in acetic acid (100 ml) was added N-chlorosuccinimide (0.97 g), and the mixture was stirred at 100° C. for 5 hours. After cooling, the reaction mixture was evaporated, and dissolved in chloroform, The solution was washed with aqueous sodium bicarbonate, and dried over magnesium sulfate. After removal of the solvent, resulting mass was crystallized from ethanol, to give 5-chloro-6-(3,4-dimethoxyphenyl)-1,3-dimethyl-1,2,3,4-tetrahydropyrimidine-2,4-dione (1.79 g).

m.p. 175°–178° C.

IR (Nujol): 1720, 1650 cm$^{-1}$.

NMR (CDCl$_3$, δ): 7.2–6.7 (3H, m), 3.94 (3H, s), 3.89 (3H, s), 3.46 (3H, s), 3.17 (3H, s)

EXAMPLE 1

To a solution of boron tribromide (25 g) in methylene chloride (100 ml) was added dropwise a solution of 3,4-dihydro-6-(3,4-dimethoxyphenyl)-1-ethyl-3-methyl-4-(2,4,6-trimethylphenylimino)-2(1H)- c pyrimidinone (10.17 g) in methylene chloride (300 ml) at −70° to −62° C. The reaction temperature was gradually raised to ambient temperature during 3 hours. After completion of the reaction, water (200 ml) was added to the reaction mixture. The aqueous layer was adjusted to pH 5.5 with an aqueous solution of sodium hydroxide. The organic layer was washed with water, dried over magnesium sulfate and evaporated. The residue was subjected to column chromatography on silica gel and eluted with a mixture of chloroform and methanol (9:1). The fractions containing the desired compound were combined and concentrated under reduced pressure to give 3,4-dihydro-6-(3,4-dihydroxyphenyl)-1- c, ethyl-3-methyl-4-(2,4,6-trimethylphenylimino)-2(1H)pyrimidinone (6.46 g).

mp : 245°–250° C. (dec.),

IR (Nujol): 1650, 1600 cm$^{-1}$.

NMR (CDCl$_3$-MeOH-d$_4$, δ): 6.45–6.90 (5H, m), 5.07 (1H, s), 3.71 (2H, q, J=7 Hz), 3.55 (3H, s), 2.20 (3H, s), 2.02 (6H, s), 1.11 (3H, t, J=7 Hz).

EXAMPLE 2

To a solution of 3,4-dihydro-6-(3,4-dihydroxyphenyl)---ethyl-3-methyl-4-(2,4,6-trimethylphenylimino)-2(1H)pyrimidinone (1.0 g) in dimethylformamide (30 ml) were added spray-dried potassium fluoride (0.77 g) and 1,2-dibromoethane (0.25 ml). The mixture was stirred at 110° C. for 2.5 hours. The reaction mixture was poured into water and extracted with diethyl ether. The organic layer was washed with water, dried over magnesium sulfate and evaporated. The residue was subjected to column chromatography on silica gel and eluted with chloroform. The fractions containing the desired compound were combined and concentrated under reduced pressure to give 3,4-dihydro-6-(3,4-ethylenedioxyphenyl)-1-ethyl-3-methyl-4-(2,4,6-trimethylphenylimino)-2(1H)-pyrimidinone (0.3 g).

mp 75°–82° C.

IR (Nujol): 1690, 1650, 1600 cm$^{-1}$.

NMR (CDCl$_3$, δ): 6.5–7.0 (5H, m), 5.04 (1H, s), 4.24 (4H, s), 3.68 (2H, q, J=7 Hz), 3.56 (3H, s), 2.21 (3H, s), 2.01 (6H, s), 1.12 (3H, t, J=7 Hz).

EXAMPLE 3

To a solution of 3,4-dihydro-6-(3,4-dihydroxyphenyl)-1-ethyl-3-methyl-4-(2,4,6-trimethylphenylimino)-2(1H)pyrimidinone (1.0 g) in dimethylformamide (30 ml) were added methylene bromide (0.21 ml) and spray-dried potassium fluoride (0.77 g). The mixture was refluxed for 3.5 hours, poured into water and extracted with diethyl ether. The organic layer was dried over magnesium sulfate and evaporated. The residue was subjected to column chromatography on silica gel and eluted with chloroform. The fractions containing the desired compound were combined and concentrated under reduced pressure. Thus obtained syrup was dissolved in 1N-hydrochloric acid (15 ml), and evaporated until 10 ml of water distilled off. The resulting crystals were collected by filtration to give 3,4-dihydro-6-(3,4-methylenedioxyphenyl)-1-ethyl-3-methyl-4-(2,4,6-trimethylphenylimino)-2(1H)-pyrimidinone hydrochloride (0.61 g).

mp : 165°–170° C.

IR (Nujol): 1710, 1640 cm$^{-1}$.

NMR (DMSO-$d_6$, $\delta$): 6.7–7.2 (5H, m), 6.10 (2H, s), 5.06 (1H, s), 3.80 (3H, s), 3.76 (2H, q, J=7 Hz), 2.24 (3H, s), 2.17 (6H, s), 1.23 (3H, t, J=7 Hz).

EXAMPLE 4

To a solution of 3,4-dihydro-6-(3,4-methylenedioxyphenyl)-1-ethyl-3-methyl-4-(2,4,6-trimethylphenylimino)-2(1H)-pyrimidinone hydrochloride (70 mg) in water (10 ml) was neutralized with an aqueous solution of sodium bicarbonate. The resulting precipitates were collected by filtration to give 3,4-dihydro-6-(3,4-methylenedioxyphenyl)-1-ethyl-3-methyl-4-(2,4,6-trimethylphenylimino)-2(1H)-pyrimidinone (60 mg).

mp : 147°–149° C.

IR (Nujol): 1690, 1650, 1600 cm$^{-1}$.

NMR (CDCl$_3$, $\delta$): 6.5–6.9 (5H, m), 5.97 (2H, s), 5.04 (1H, s), 3.68 (2H, q, J=7 Hz), 3.56 (3H, s), 2.20 (3H, s), 2.00 (6H, s), 1.10 (3H, t, J=7 Hz).

EXAMPLE 5

To a solution of 3,4-dihydro-6-(3,4-dihydroxyphenyl)-1-ethyl-3-methyl-4-(2,4,6-trimethylphenylimino)-2(1H)-pyrimidinone (1.0 g) in benzene (50 ml) were added 2,2-dimethoxypropane (2.1 ml) and p-toluenesulfonic acid monohydrate (0.05 g). The solution was refluxed for 4 hours. And then an additional 2,2-dimethoxypropane (2.1 ml) and p-toluenesulfonic acid monohydrate (0.5 g) were added thereto, and the reaction mixture was refluxed for more 13 hours. After being cooled, the reaction mixture was added to ethyl acetate and the solution was washed with an aqueous solution of sodium bicarbonate. The organic layer was dried over magnesium sulfate and evaporated. The residue was subjected to column chromatography on silica gel and eluted with chloroform. The fractions containing the desired compound were combined and concentrated under reduced pressure. Thus obtained syrup was dissolved in 1-N-hydrochloric acid. After filtration, the solution was neutralized with an aqueous solution of sodium bicarbonate. The resulting precipitates were collected by filtration to give 3,4-dihydro-6-(3,4-isopropylidenedioxyphenyl)-1-ethyl-3-methyl-4-(2,4,6-trimethylphenylimino)-2(1H)-pyrimidinone (0.51 g).

mp : 67°–77° C.

IR (Nujol): 1695, 1650, 1600 cm$^{-1}$.

NMR (CDCl$_3$, $\delta$): 6.5–6.9 (5H, m), 5.04 (1H, s), 3.70 (2H, q, J=7 Hz), 3.56 (3H, s), 2.21 (3H, s), 2.01 (6H, s), 1.66 (6H, s), 1.11 (3H, t, J=7 Hz).

EXAMPLE 6

To a suspension of 1,3-dimethyl-6-(4-methoxy-3-methylthiophenyl)-1,2,3,4-tetrahydro-4-thioxopyrimidine-2-one (5.0 g) in tetrahydrofuran (50 ml) was added methyl iodide (20 ml), and refluxed for an hour. After cooled, the resulting precipitates were collected by filtration. To the precipitate was added 2,4,6trimethylaniline (9.5 ml), and stirred at 100° C. for 3 hours. After cooled, the mixture was triturated with n-hexane, and the resulting precipitate was dissolved in chloroform. The solution was washed with aqueous sodium bicarbonate solution, dried over magnesium sulfate, and chromatographed on silica gel, eluting with chloroform. The obtained syrup was dissolved in 1-N-hydrochloric acid, and neutralized by aqueous sodium bicarbonate solution. The obtained powders were crystallized from diisopropyl ether to give 3,4-dihydro-6-(4-methoxy-3-methylthiophenyl)-1,3-dimethyl-4-(2,4,6-trimethylphenylimino)-2(1H)-pyrimidinone (4.9 g).

mp 147°–149° C.

IR (Nujol): 1690, 1645, 1600 cm$^{-1}$.

NMR (DMSO-$d_6$, $\delta$): 7.0–7.2 (3H, m), 6.86 (2H, s), 4.84 (1H, s), 3.80 (3H, s), 3.45 (3H, s), 3.05 (3H, s), 2.33 (3H, s), 2.14 (3H, s), 1.93 (6H, s).

EXAMPLE 7

The following compounds were prepared according to the similar manner to that of Example 6.

(1) 3,4-Dihydro-6-(4-methoxy-3-methylsulfinylphenyl)-1,3-dimethyl-4-(2,4,6-trimethylphenylimino)-2(1H)pyrimidinone.

mp 125°–135° C.

IR (Nujol): 1690, 1650 cm$^{-1}$.

(2) 3,4-Dihydro-6-(4-methoxy-3-methylsulfonylphenyl)-1,3-dimethyl-4-(2,4,6-trimethylphenylimino)-2(1H)pyrimidinone.

mp 120°–130° C.

IR (Nujol): 1690, 1645 cm$^{-1}$.

EXAMPLE 8

To a solution of 3,4-dihydro-6-(4-methoxy-3-methylthiophenyl)-1,3-dimethyl-4-(2,4,6-trimethylphenylimino)-2(1H)-pyrimidinone (1.5 g) in N,N-dimethylformamide (15 ml) was added m-chloroperbenzoic acid (1.58 g), and stirred at 5°–10° C. for 30 minutes, and at ambient temperature for 5 hours. To the reaction mixture was added water (50 ml), and extracted with ethyl acetate. The organic layer was washed with aqueous sodium bicarbonate solution, dried over sodium sulfate, and evaporated. The residue was chromatographed on silica gel, eluting with chloroform. The fractions containing a sulfonyl compound were collected, dissolved in 1-N-hydrochloric acid and neutralized by aqueous sodium bicarbonate solution to give powdery 3,4-dihydro-6-(4- ro methoxy-3-methylsulfonylphenyl)-1,3-dimethyl-4-(2,4,6-trimethylphenylimino)-2(1H)-pyrimidinone (0.78 g).

mp 120°–130° C.

IR (Nujol): 1690, 1645 cm$^{-1}$.

NMR (CDCl$_3$, $\delta$): 7.82 (1H, d, J=2 Hz), 7.40 (1H, dd, J=2 Hz, J=8 Hz), 7.04 (1H, d, J=8 Hz), 6.79 (2H, s), 5.09 (1H, s), 4.00 (3H, s), 3.57 (3H, s), 3.20 (3H, s), 3.11 (3H, s), 2.20 (3H, s), 2.00 (6H, s).

Other fractions containing a sulfinyl compound were collected, dissolved in 1-N-hydrochloric acid and neutralized by aqueous sodium bicarbonate solution to give powdery 3,4-dihydro-6-(4-methoxy-3-methylsulfinylphenyl)-1,3-dimethyl-4-(2,4,6-trimethylphenylimino)-2(1H)pyrimidinone (0.34 g). mp 125°–135° C.

IR (Nujol): 1690, 1650 cm$^{-1}$.

NMR (CDCl$_3$, δ): 7.60 (1H, d, J=2 Hz), 7.38 (1H, dd, J=2 Hz, J=8 Hz), 7.05 (1H, d, J=8 Hz), 6.81 (2H, s), 5.15 (1H, s), 3.94 (3H, s), 3.57 (3H, s), 3.16 (3H, s), 2.81 (3H, s), 2.21 (3H, s), 2.03 (6H, s).

EXAMPLE 9

To 2.5 ml of chlorosulfonic acid cooled in ice bath was gradually added 3,4-dihydro-6-(3,4-dimethoxyphenyl)-1-ethyl-3-methyl-4-(2,4,6-trimethylphenylimino)-2(1H)-pryrimidinone (3.0 g). The mixture was stirred at ambient temperature for 1.5 hours, and poured into an ice-cooled aqueous ammonia (28%, 50 ml). After the resultant mixture was stirred for 2 hours, chloroform (50 ml) was added thereto. The separated organic layer was dried over sodium sulfate and evaporated.

The resulting mass was chromatographed on silica gel eluting with a mixture of chloroform methanol (50:1 v/v–9:1 v/v), to give 3, 4-dihydro-6-(4,5-dimethoxy-2-sulfamoylphenyl)-1-ethyl-3-methyl-4-(3-sulfamoyl-2,4,6-trimethylphenylimino)-2(1H)-pyrimidinone (0.28 g).

m.p. 173°–178 ° C.

IR(Nujol) 1640 cm$^{-1}$.

NMR(CDCl$_3$-MeOH -d$_4$, δ): 7.46(1H, s), 6.90(1H, s), 6.66 (1H, s) 4.96(1H, s),3.91(3H, s) 3.87(3H, s) 3.70(2H, q, J=7 Hz) 3.57(3H, s) 2.53(3H, s) 2.37(3H, s) 2.06(3H, s) 1.15 (3H, t, J=7 Hz).

EXAMPLE 10

To a suspension of 3,4-dihydro-6-(3,4-dimethoxyphenyl)-3-methyl-4-(2,4,6-trimethylphenylimino)-2(1H)-pyrimidinone (26.1 g) in N,N-dimethylformamide (350 ml) were added potassium tert. butoxide (9.2 g) and ethyl bromoacetate (13.7 g) at room temperature. The mixture was stirred overnight. After neutralization with diluted hydrochloric acid, the mixture was evaporated and chromatographed on silica gel using chloroform. Fractions containing the object compound were evaporated and the residue was triturated in ethanol to give 3,4-dihydro-6-(3,4-dimethoxyphenyl)-1-ethoxycarbonylmethyl-methyl-4(2,4,6-trimethylphenylimino)-2(1H)pyrimidinone (15.3 g). mp. 112°–113° C.

IR (Nujol): 1745, 1692, 1645 cm$^{-1}$.

NMR (DMSO-d$_6$, δ): 1.15 (3H, t, J=7.5 Hz), 1.95 (6H, s), 2.17 (3H, s), 3.46 (3H, s), 3.70 (3H, s), 3.75 (3H, s), 4.10 (2H, q, J=7.5 Hz), 4.28 (2H, s), 4.91 (1H, s), 6.67–7.07 (5H, m)

EXAMPLE 11

To a solution of 3,4-dihydro-6-(3,4-dimethoxyphenyl)-1-ethoxycarbonylmethyl-3-methyl-4-(2,4,6-trimethylphenylimino)-2(1H)-pyrimidinone (4 g) in methanol (30 ml) was added a solution of sodium hydroxide (0.52 g) in water (6 ml) and stirred at room temperature for 3 hours. After removal of methanol, the residue was dissolved in water (40 ml) and adjusted to pH 5.8 and extracted with chloroform. The chloroform layer was washed with brine, dried over magnesium sulfate and evaporated to give a residue, which was triturated in n-hexane to give colorless powders (3.3 g) of 3,4-dihydro-1-carboxymethyl-6-(3,4-dimethoxyphenyl)-3-methyl-4-(2,4,6-trimethylphenylimino)-2(1H)-pyrimidinone.

mp. 148°–150° C.

IR (KBr): 1720, 1685, 1660, 1240 cm$^{-1}$.

NMR (DMSO-d$_6$, δ): 2.00 (6H, s), 2.19 (3H, s), 3.50 (3H, s), 3.73 (3H, s), 3.78 (3H, s), 4.20 (2H, s), 4.93 (1H, s), 6.68–7.06 (5H, m).

EXAMPLE 12

To a solution of 3,4-dihydro-1,3-dimethyl-6-(4-methoxy-3-nitrophenyl)-4-(2,4,6-trimethylphenylimino)-2(1H)-pyrimidinone (0.94 g) in a mixture of methanol (20 ml) and conc. hydrochloric acid (0.4 ml) was added palladium on activated carbon (10%, 0.20 g). The mixture was stirred under hydrogen atmosphere (1 atm) for 2 hours, and filtered. The filtrate was poured into aqueous sodium bicarbonate, and extracted with chloroform. The organic layer was dried over sodium sulfate, and evaporated. The resulting mass was crystallized from ethanol, to give 3,4-dihydro-6-(3-amino-4-methoxyphenyl)-1,3-dimethyl-4-(2,4,6-trimethylphenylimino)-2(1H)-pyrimidinone (0.63 g).

mp. 176°–178° C.

IR (Nujol): 1680, 1650, 1600 cm$^{-1}$.

NMR (CDCl$_3$, δ): 6.9–6.4 (5H, m), 5.10 (1H, s), 3.9 (2H, br. s), 3.87 (3H, s), 3.60 (3H, s), 3.18 (3H, s), 2.25 (3H, s), 2.03 (6H, s).

EXAMPLE 13

To a solution of 3,4-dihydro-6-(3-amino-4-methoxyphenyl)-1,3-dimethyl-4-(2,4,6-trimethylphenylimino)-2(1H)-pyrimidinone (0.39 g) in 1,2-dichloroethane (5 ml) were added methanesulfonyl chloride (0.40 ml) and triethylamine (0.52 ml) successively, and the mixture was refluxed for 2.5 hours. After cooling, the reaction mixture was dissolved in chloroform, and washed with water. The organic layer was dried over magnesium sulfate, evaporated, and crystallized from ethanol to give 3,4-dihydro-6-[3-(dimethanesulfonylamino)-4methoxyphenyl]-1,3-dimethyl-4-(2,4,6-trimethylphenylimino)-2-(1H)-pyrimidinone (0.33 g).

m.p. 183°–186° C.

IR (Nujol): 1650, 1595 cm$^{-1}$.

NMR (CDCl$_3$, δ): 7.5–6.7 (5H, m), 5.13 (1H, s), 3.71 (3H, s), 3.56 (3H, s), 3.36 (6H, s), 3.12 (3H, s), 2.21 (3H, s), 2.01 (6H, s).

EXAMPLE 14

A solution of 3,4-dihydro-6-(3,4-dimethoxyphenyl)-1,3-dimethyl-4-(2,4,6-trimethylphenylimino)-2(1H)pyrimidinone (5.0 g) in aqueous hydrobromic acid (47%) (50 ml) was refluxed for 1.5 hours. After being cooled to ambient temperature, the solution was neutralized with aqueous sodium hydroxide, and extracted with chloroform. The organic layer was washed with brine, dried over sodium sulfate, and evaporated. The resulting oil was crystallized from a mixture of diisopropyl ether and ethyl acetate (1:1 v/v) to give 3,4-dihydro-6-(3,4-dihydroxyphenyl)-1,3-dimethyl-4-(2,4,6-trimethylphenylimino)-2(1H)-pyrimidinone (4.41 g).

m.p. 222°–225° C.

IR (Nujol): 1660, 1640, 1590 cm$^{-1}$.

NMR (CDCl$_3$, δ): 7.0–6.0 (7H, m), 5.14 (1H, s), 3.65 (3H, s), 3.16 (3H, s), 2.23 (3H, s), 2.07 (6H, s).

EXAMPLE 15

To a solution of 3,4-dihydro-6-(3,4-dihydroxyphenyl)-1,3-dimethyl-4-(2,4,6-trimethylphenylimino)-2(1H)pyrimidinone (2.0 g) in N,N-dimethylformamide (20 ml) were added sodium hydride (60% in Nujol, 0.22 g) and methyl iodide (0.37 ml), and the mixture was stirred at ambient temperature for 2 hours. Then the reaction mixture was poured into water (200 ml), and extracted with ethyl acetate. The organic extract was washed with brine, dried over magnesium sulfate and evaporated. The residue was chromatographed on silica gel eluting with chloroform to give 3,4-dihydro-1,3-dimethyl-6-(4-hydroxy-3-methoxyphenyl)-4-(2,4,6-trimethylphenylimino)-2(1H)-pyrimidinone (0.66 g).

m.p. 90°–100° C.

IR (Nujol): 1650 cm$^{-1}$.

NMR (CDCl$_3$, δ): 7.0–6.5 (5H,m), 5.09 (1H, s), 3.89 (3H, s), 3.59 (3H, s), 3.16 (3H, s), 2.20 (3H, s), 2.02 (6H, s).

EXAMPLE 16

To a solution of 3,4-dihydro-1,3-dimethyl-6-(4-hydroxy-3-methoxyphenyl)-4-(2,4,6-trimethylphenylimino)-2(1H)-pyrimidinone (0.40 g) in acetone (20 ml) were added potassium carbonate (0.16 g) and ethyl bromoacetate (0.66 ml), and the mixture was refluxed for 10 hours. After being cooled, the mixture was evaporated and suspended in chloroform. The suspension was washed with water, dried over sodium sulfate, and evaporated to give crude oil of 3,4-dihydro-1,3-dimethyl-6-(4-ethoxycarbonylmethoxy-3-methoxyphenyl)-4-(2,4,6-trimethylphenylimino)-2(1H)-pyrimidinone (0.67 g). This crude oil was used for the following deesterification without further purification.

EXAMPLE 17

To a solution of 3,4-dihydro-1,3-dimethyl-6-(4-ethoxycarbonylmethoxy-3-methoxyphenyl)-4-(2,4,6-trimethylphenylimino)-2(1H)-pyrimidinone as obtained in Example 16 (0.67 g) in methanol (4 ml) was added 1N aqueous sodium hydroxide (2.38 ml) and the mixture was stirred at ambient temperature for 2 hours. After removal of the solvent, the residue was dissolved in water (5 ml), neutralized with 1-Nhydrochloric acid and extracted with chloroform. The organic layer was dried over sodium sulfate, evaporated, and triturated in diisopropyl ether to give 3,4-dihydro-6-(4-carboxymethoxy-3-methoxyphenyl)-1,3-dimethyl-4-(2,4,6-trimethylphenylimino)-2(1H)-pyrimidinone (0.47 g).

m.p. 170°–180° C.

IR (Nujol): 1690, 1650 cm$^{-1}$.

NMR (CDCl$_3$, δ): 6.80 (2H, s), 6.30–6.60 (3H, m), 5.55 (2H, br. s), 4.98 (1H, s), 3.65 (3H, s), 3.57 (3H, s), 3.03 (3H, s), 2.19 (3H, s), 2.04 (6H, s).

EXAMPLE 18

The following compound was obtained according to a similar manner to that of Example 6. 3,4-Dihydro-1,3-dimethyl-6-(4-methoxy-3-nitrophenyl)-(2,4,6-trimethylphenylimino)-2(1H)-pyrimidinone.

m.p. 115°–120° C.

IR (Nujol): 1690, 1655 cm$^{-1}$.

NMR (CDCl$_3$,δ): 7.71 (1H, d, J=2 Hz), 7.43 (1H, dd, J=2 Hz, J=8 Hz), 7.10 (1H, d, J=8 Hz), 6.86 (2H, s), 5.14 (1H, s), 3.99 (3H, s), 3.60 (3H, s), 3.17 (3H, s), 2.23 (3H, s), 2.04 (6H, s).

EXAMPLE 19

To a solution of 3,4-dihydro-6-(3,4-dihydroxyphenyl)-1-ethyl-3-methyl-4-(2,4,6-trimethylphenylimino)-2(1H)pyrimidinone (1.0 g) in dioxane (25 ml) and ethanol (5 ml), was bubbled chlorodifluoromethane at 10° C. for 5 minutes. Then 4N-aqueous sodium hydroxide solution (8.0 ml) was added. The solution was stirred with bubbling by chlorodifluoromethane at 10° C. for 1 hour, and at ambient temperature for 3 hours. Then the mixture was evaporated, and extracted by ethyl acetate. The organic layer was washed by water, dried over sodium sulfate, and chromatographed on silica gel eluting with chloroform, to give 3,4-dihydro-6-[3,4-bis(difluoromethoxy)phenyl]-1-ethyl-3-methyl-4-(2,4,6-trimethylphenylimino)-2(1H)pyrimidinone (0.47 g).

m.p. 145°–148° C.

IR (Nujol): 1670, 1650 cm$^{-1}$.

NMR (CDCl$_3$, δ): 7.0–7.4 (3H, m), 6.80 (2H, br, s) 6.53 (2H, t, J$_{hf}$=72 Hz), 5.07 (1H, s), 3.63 (2H, q, J=7 Hz), 3.59 (3H, s), 2.22 (3H, s), 2.03 (6H, s), 1.11 (3H, t, J=7 Hz).

EXAMPLE 20

To a suspension of 3,4-dihydro-6-3,4-dimethoxyphenyl)-3-methyl-4-(2,4,6-trimethylphenylimino)-2(1H)pyrimidinone (1.0 g) in N,N-dimethylformamide (20 ml) were added 1-chloro-3-dimethylaminopropane hydrochloride (4.17 g) and potassium carbonate (7.28 g), and was stirred at 100° C. for 12 hours. After cooled, the mixture was poured into water (200 ml), and extracted by ethyl acetate. The organic layer was washed with brine, dried over sodium sulfate, evaporated in vacuo, and chromatographed on silica gel using chloroform-methanol mixture (49:1 v/v), to give 3,4-dihydro-6-(3,4-dimethoxyphenyl)-1-(3-dimethylaminopropyl)-3-methyl-4(2,4,6-trimethylphenylimino)-2(1H)-pyrimidinone (0.62 g).

IR (Nujol): 1590, 1640, 1685 cm$^{-1}$.

NMR (CDCl$_3$, δ): 6.6–6.9 (5H, m), 5.06 (1H, s), 3.85 (3H, s), 3.83 (3H, s), 3.56 (3H, s), 3.5–3.8 (2H, m), 2.19 (3H, s), 2.0–2.4 (2H, m), 2.06 (6H, s), 2.01 (6H, s), 1.8–1.5 (2H, m).

What we claim is:

1. Pyrimidinone compounds of the formula:

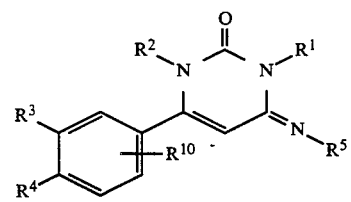

wherein

R$^1$ and R$^2$ are each lower alkyl, lower alkoxycarbonyl (lower) alkyl, carboxy (lower) alkyl or di(lower) alkylamino (lower) alkyl, R$^3$ is hydroxy, lower alkoxy, halo (lower) alkoxy, lower alkylthio, lower alkanesulfinyl, lower alkanesulfonyl, nitro, amino or di(lower) alkanesulfonylamino, R$^4$ is hydroxy, lower alkoxy, halo (lower) alkoxy, lower alkoxycarbonyl (lower) alkoxy or carboxy(lower)alkoxy, or $R^3$ and $R^4$ are taken together to form lower alkylendedioxy or lower alkylidenedioxy, $R^5$ is phenyl substituted with 1 to 4 substituents selected from the group consisting of lower alkyl and sulfamyl, $R^{10}$ is hydrogen or sulfamyl, provided that when both of $R^1$ and $R^2$ are lower alkyl and $R^3$ and $R^4$ are lower alkoxy, then $R^{10}$ is sulfamoyl, and that when $R^3$ is hydroxy, then $R^4$ is hydroxy, and pharmaceutically acceptable salts thereof.

2. A compound of claim 1, wherein $R^1$ and $R^2$ are each methyl, ethyl, ethoxycarbonylmethyl, carboxymethyl, or dimethylaminopropyl, $R^3$ is hydroxy, methoxy, difluoromethoxy, methylthio, methylsulfinyl, methlsulfonyl, nitro, amino or dimethanesulfonylamino, $R^4$ is hydroxy, methoxy, difluoromethoxy, ethoxycarbonylemthoxy or carboxymethoxy, or $R^3$ and $R^4$ are taken together to form ethylenedioxy, methylenedioxy or isopropylidenedioxy, $R^5$ is phenyl substituted with 1 to 4 substituents selected from the group consisting of methyl and sulfamyl, and $R^{10}$ is hydrogen or sulfamyl, provided that when $R^1$ is methyl and $R^2$ is methyl or ethyl and $R^3$ and $R^4$ are methoxy, then $R^{10}$ is sulfamyl, and that when $R^3$ is hydroxy, then $R^4$ is hydroxy.

3. A compound of claim 2, wherein $R^1$ is methyl, $R^2$ is methyl, ethyl, ethoxycarbonylmethyl, carboxymethyl or dimethylaminopropyl, and $R^5$ is phenyl substituted with tri-methyl or with tri-methyl and mono-sulfamyl.

4. A cardistonic pharmaceutical composition comprising, as an active ingredient, a cardiotonically effective amount of the compound of claim 1, in association with a non-toxic, pharmaceutically acceptable carrier or excipient.

5. An antiallergic pharmaceutical composition comprising, as an active ingredient, an antiallergically effective amount of the compound of claim 1, in association with a non-toxic, pharmaceutically acceptable carrier or excepient.

6. A method of treating heart disease which comprises administering to a subject in need of such treatment a cardiotonically effective amount of the compound of claim 1.

* * * * *